United States Patent [19]
Martin

[11] Patent Number: 5,985,546
[45] Date of Patent: *Nov. 16, 1999

[54] STEALTH VIRUS DETECTION IN THE CHRONIC FATIGUE SYNDROME

[76] Inventor: William John Martin, 1634 Spruce St., Pasadena, Calif. 91030

[*] Notice: This patent is subject to a terminal disclaimer.

[21] Appl. No.: 09/085,271

[22] Filed: May 26, 1998

Related U.S. Application Data

[63] Continuation of application No. 08/157,811, Nov. 23, 1993, Pat. No. 5,756,281, which is a continuation-in-part of application No. 07/887,502, May 22, 1992, abandoned, which is a continuation-in-part of application No. 07/704,814, May 23, 1991, abandoned, and application No. 07/763,039, Sep. 20, 1991, abandoned.

[51] Int. Cl.$^6$ .................................................. C12Q 1/70
[52] U.S. Cl. ................................................................ 435/5
[58] Field of Search .............................. 435/5, 325, 239, 435/91.1, 91.2, 4

[56] References Cited

U.S. PATENT DOCUMENTS

| | | | |
|---|---|---|---|
| 4,683,195 | 7/1987 | Mullis et al. | 530/6 |
| 4,683,202 | 7/1987 | Mullis | 435/91.2 |
| 4,889,818 | 12/1989 | Gelfand et al. | 435/194 |
| 5,703,221 | 12/1997 | Martin | 435/5 |

FOREIGN PATENT DOCUMENTS

92/20787  11/1992  WIPO .

OTHER PUBLICATIONS

Ablashi et al., "Genomic Polymorphism, growth properties and immunologic variations in human herpesvirus 6 isolates," *Virology* 184:545–552 (1991).
Ablashi et al., "Utilization of human hematopoietic cell lines for the propagation and characterization of HBLV (Human Herpesvirus 6)," *Int. J. Cancer* 42:787–791 (1988).
Archard et al., "Postviral fatigue syndrome: persistence and enterovirus RNA in muscle and elevated creatine kinase," *The Royal Society of Medicine* vol. 81 (1988).
Buchwald et al. "A chronic illness characterized by fatigue, neurologic and immunologic disorders and active human herpesvirus type 6 infection," *Annals of Internal Medicine* 116:103–113 (1992).
Chee et al., "Analysis of the protein coding content of the sequence of human cytomegalovirus strain AD169," *Current Topics in Microbiology and Immunology* 154:126–169 (1990).
Cohen et al., "Okadaic acid: A new probe for the study of cellular regulation," *TIBS* 15:98–102 (1990).
Cowley et al., "A chronic fatigue cover–up," *Newsweek* p. 62 (1996).
Dale et al., "The Inoue–Melnick virus, human herpesvirus type 6, and the chronic fatigue syndrome," *Annals of Internal Medicine* 110:92–93 (1989).
Dale et al., "Chronic fatigue syndrome: Lack of association with hepatitis C virus infection," *J. Medical Virology* 34:119–121 (1991).
DeFreitas et al., "Retroviral sequences related to human T–lymphotropic virus type II in patients with chronic fatigue immune dysfunction syndrome," *Chemical Abstracts* 114:No. 205331c (1991).
DeFreitas et al., "Retroviral sequences related to human T–lymphotropic virus type II in patients with chronic fatigue immune dysfunction syndrome," *Proc. Natl. Acad. Sci. USA* 88:2922–2926 (1991).
Demitrack et al,. "Evidence for impaired activation of the hypothalamic–pituitary–adrenal axis in patients with chronic fatigue syndrome," *Journal of Clinical Endrocrinology and Metabolism* 73:1224–1234 (1991).
DiLuca et al., "The replication of viral and cellular DNA in human herpesvirus 6–infected cells," *Virology* 175:199–210 (1990).
Ehrlich et al., "Detection of human T–cell lymphoma–leukemia viruses," *PCR Protocols: A Guide to Methods and Applications*, Ch. 39, pp. 325–336 (1990).
Feinberg et al., "A technique for radiolabeling DNA restriction endonuclease fragment to high specific acitivity," *Anal. Biochem.* 137:266–267 (1984).
Freshney, "Ch. 10– Maintenance of the culture–cell lines," *Culture of Animal Cells: a Manual of Basic Technique*, Alan R. Liss, Inc., New York, pp. 127–136 (1987).
Gupta et al., "A comprehensive immunological analysis in chronic fatigue syndrome," *Scand. J. Immunol.* 33:319–327 (1991).
Ham, R.G., "An improved nutrient solution for diploid chinese hamster and human cell lines," *Exp. Cell Research* 29:515–526 (1963).
Ho, M. *Cytomegalovirus: Biology and Infection*, $2^{nd}$ ed., pp. 75–76, Plenum Medical Book Company, New York, N.Y. (1991).
Holmes, G.P., "Defining the chronic fatigue syndrome," *Reviews of Infectious Diseases* 13(Suppl. 1.)553–555 (1991).
Holmes et al., "Chronic fatigue syndrome: A working case definition," *Annals of Internal Medicine* 108:387–389 (1988).
Iscove et al., "Complete replacement of serum by albumin, transferrin and soybean lipid in cultures of lipopolysaccharide–reactive B lymphocytes," *J. Exp. Med.* 147:923–933 (1978).
Kendell, R.E., "Chronic fatigue viruses and depression," *The Lancet* 337:160–161 (1991).

(List continued on next page.)

*Primary Examiner*—Nancy Degen
*Assistant Examiner*—Vem Tucel
*Attorney, Agent, or Firm*—Lyon & Lyon LLP

[57] ABSTRACT

A method of detecting a stealth virus is provided by culturing a sample under conditions in which any stealth virus in the sample is able to induce a cytopathic effect. A method for culturing a virus is also provided by (a) cocentrifuging a sample of said virus with a permissive cell line of indicator cells; (b) inoculating the cell mixture into culture vessels; (c) adding viral enhancing medium to the culture; and (d) detecting in vitro a cytopathic effect in the permissive cell line.

25 Claims, No Drawings

OTHER PUBLICATIONS

Landay et al., "Chronic fatigue syndrome: Clinical condition associated with immune activation," *The Lancet* 338:707–712 (1991).

Martin, W.J., "Ch. 27–Detection of viral related sequences in CFS patients using the polymerase chain reaction," *The Clinical and Scietific Basis of Myalgic Encephalomyelitis/Chronic Fatigue Sydrome*, pp. 278–281, Hyde et al., eds., The Nightingale Research Foundation, Ogdensburg, New York (1992).

Niks et al., "Towards an optimized MTT assay," *Immunological Methods* 130:149–151 (1990).

Palca, J., "On the track of an elusive disease, " *Science* 254:1726–1728 (1991).

Palca, J., "Does a retrovirus explain fatigue syndrome puzzle?" *Science* 249:1240–1241 (1991).

Rethwilm et al., "Infectious DNA of the human spumaretrovirus," *Nucleic Acids Research* 18:733–738 (1990).

Schirmer et al., "Differentiation between two distinct classes of viruses now classified as human herpesvirus 6," *Proc. Natl. Acad. Sci. USA* 88:5922–5926 (1991).

Shafran, S.D., "The chronic fatigue syndrome," *The American Journal of Medicine* 90:730–738 (1991).

Shepherd, C., "Myalgic Encephalomyelitis—Is it a real disease?" *The Practitioner* 233:41–46 (1989).

Sundin et al., *J. Clin. Microbiol.* 27(7):1659–1660 (1989).

Welch et al., "Cytomegalovirus homologs of cellular G protein–coupled receptor genes are transcribed," *J. Virology* 65:3915–3918 (1991).

Werner, J., "Isolation of foamy virus from patients with De Quervain Thyroiditis," *The Lancet* 11:258–259 (1979).

Yousef et al., "Chronic enterovirus infection in patients with postviral fatigue syndrome," *The Lancet* I:146–150 (1988).

STEALTH VIRUS DETECTION IN THE CHRONIC FATIGUE SYNDROME

This application is a continuation of U.S. patent application Ser. No. 08/157,811, filed Nov. 23, 1993, now U.S. Pat. No. 5,756,281, which is a continuation-in-part of U.S. patent application Ser. No. 07/887,502, filed May 22, 1992, now abandoned, which is a continuation-in-part of U.S. patent application Ser. No. 07/704,814, filed May 23, 1991, now abandoned and U.S. patent application Ser. No. 07/763,039, filed Sep. 20, 1991, now abandoned.

1. FIELD OF INVENTION

The present invention relates generally to methods for detecting the presence of a virus. More particularly, it relates to the detection of viruses by tissue culture techniques.

2. BACKGROUND OF THE INVENTION

A. Chronic Fatigue Syndrome

Palca, *Science,* 249:1240–1241 (1990) and Palca, *Science,* 254:1726–1728 (1991) describe attempts to identify a causative agent for chronic fatigue syndrome.

DeFreitas et al., *Chemical Abstracts,* 114: Abstract No. 205331c (1991) describes retroviral sequences related to human T lymphotropic virus type 2 in patients with chronic fatigue immune dysfunction syndrome.

Gupta et al., *Scandinavian Journal of Immunology,* 33:319–327 (1991) describes a comprehensive immunological analysis of chronic fatigue syndrome. The analysis of cell mediated and antibody mediated immunity was performed in 20 patients with chronic fatigue syndrome and 20 age and sex matched healthy controls.

B. Culture Techniques

Werner, *Lancet,* II:258–259 (1979) describes the isolation of foamy viruses from patients with de Quervain Thyroiditis and the detection of a cytopathic effect.

Freshney, *Culture of Animal Cells: A Manual of Basic Technique,* pp. 127–136 (Alan R. Liss Inc., 1987) describes the maintenance of cell cultures and states that four factors indicate the need for replacement of culture medium: (1) a drop in pH; (2) high cell concentration; (3) cell types such as transformed cells, continuous cell lines and some embryonic cells that deteriorate rapidly at high cell densities; and (4) morphological deterioration of the cell such as granularity around the nucleus, cytoplasmic vacuolation, and rounding up of the cells with detachment from the substrate.

DiLuca et al., *Virology,* 175:199–210 (1990) describes the replication of viral and cellular DNA in human herpesvirus 6-infected cells and the use of medium RPMI 1640 containing 10% fetal calf serum.

Ablashi et al., *International Journal of Cancer,* 42:787–791 (1988) describes the use of human hematopoietic cell lines for the propagation of HBLV (human herpesvirus 6) in RPMI 1640 supplemented with 10% FBS and antibiotics.

Rethwilm et al., *Nucleic Acids Research,* 18:733–738 (1990) describes an infectious molecular clone (pHSRV) of the human spumaretrovirus (HSRV). pHSRV derived virus produced foamy virus typical cytopathie effects in susceptible cultures.

3. SUMMARY OF THE INVENTION

The present invention provides a method for detecting a stealth virus by culturing a sample under conditions that induce a cytopathic effect. Several culture conditions are sufficient to induce a cytopathic effect in a sample containing a stealth virus. These culture conditions include replacing the culture medium every 24 to 72 hours, adding 5% to 10% fetal calf serum to the culture medium, using serum free medium X Vivo-15, using preculture centrifugation and adding viral enhancing medium to the culture.

In one aspect, a method of detecting a stealth virus is provided by culturing a sample under conditions in which any stealth virus in the sample is able to induce a cytopathic effect.

The term "stealth virus" refers to a virus having all of the following characteristics: (a) the ability to induce a cytopathic effect in fibroblastic cultures including primary kidney cell cultures which is characterized by the production of foamy appearing cells, including cell syncytia; (b) the ability to produce a toxin capable of suppressing viral growth; (c) the ability to grow in cells from a plurality of species; (d) the inability of viral infected cells to react in a typical manner using typing antisera specific for cytomegalovirus, herpes simplex virus, varicella zoster virus, Epstein-Barr virus and human T cell lymphotropic virus (HTLV); (e) the inability of viral infected cells to hybridize in a typical manner with nucleic acids probes specific for HTLV, cytomegalovirus, herpes simplex virus, human herpes virus-6, varicella zoster virus and Epstein-Barr viruses using stringent hybridization conditions; and (f) the inability to evoke an inflammatory response in tissues which it infects.

The term "cytopathic effect" (CPE) refers to the appearance of rounded, slightly enlarged, retractile cells throughout the culture. In some cultures the CPE progresses to very prominent collections of tightly packed, enlarged, foamy-cell appearing cells, with clearly defined cell syncytia and evidence of considerable cell destruction. Stages between the spindle shape of the normal fibroblasts and the rounded appearance of affected cells can be seen. Several inclusions, consistent with vacuoles, can been seen within the cytoplasm. As their numbers increase, affected cells form several tightly adherent clumps with indistinct cell boundaries. The affected cells continue to proliferate and scatter away from the cell clumps.

In preferred embodiments the presence of the stealth virus is detected by (1) inoculating a permissive cell line with a sample, and (2) detecting in vitro a CPE in the permissive cell line; the cell line is maintained in culture medium that is replaced every 24 to 72 hours; the cell line is an insect cell line e.g., the cell line is derived from a plurality of species and may even include *Spodoptera fruiperdo* derived ovarian cell line Sf9; and the sample is from a patient suspected of having chronic fatigue syndrome (CFS) based upon other recognized criteria well known to physicians in the art.

The term "chronic fatigue syndrome" (CFS) refers to an illness whose major characteristic is an unexplained fatigue lasting beyond 6 months which results in greater than 50% reduction in an individual's normal level of activity (Holmes et al., "Chronic fatigue syndrome: A working case definition," *Ann. Intern. Med.,* 108:387–389 (1988); Holmes, "Defining the chronic fatigue syndrome", *Rev. Inf. Dis.,* 13 (Suppl. I):S53–5 (1991); Shafan, "The chronic fatigue syndrome" *Am. J. Med.,* 90:731–738 (1991)). To establish a clinical diagnosis, the patients should show evidence of suffering at least eight of the following minor symptoms: fever, sore throat, myalgia, muscle weakness (which may be exacerbated by exercise), arthralgia, lymphadenopathy, sleep disturbance, headaches, acute or subacute onset, and neuropsychological symptoms. The neuropsychological symptoms include a difficulty in thinking, dysnomia, confusion, forgetfulness, irritability, depression, photophobia and transient visual scotomata.

A cell is "permissive" if a particular virus causes a productive infection in it. A productive infection is a viral infection of a cell that produces progeny with the vegetative or lytic cycle. A productive infection by a stealth virus is characterized by the appearance of a cytopathic effect. Using appropriate conditions, stealth viruses infect and propagate in many mammalian cells in vitro, especially cultures of fibroblastic cells including primary kidney cell cultures, and other cell lines of epidermal, mesodermal, neuroectodermal and lymphoid origin, e.g., glial cells, myoblasts, etc. The distinctive CPE is, however, readily observed in primary fibroblast cultures. At present, therefore, these are the preferred cell lines to isolate the virus from clinical and animal samples. Suitable cells include human MRC-5 lung fibroblasts, primary human foreskin fibroblasts MRHF and rhesus monkey kidney RMK cells. These well known cell lines are available commercially (e.g., from Whittaker Bioproducts, Walkersville, Md.). It should be noted that not all cell lines are permissive for growth and/or for the expression of a cytopathic effect (CPE). Conversely, other cell lines may be more efficient in promoting the growth of stealth viruses than the fibroblast cell lines currently used. The tissue culture cell lines are maintained in the laboratory using methods well known in the art.

In a second aspect a method of detecting a stealth virus is provided by: (1) inoculating a permissive cell line with a sample; (2) neutralizing stealth virus-associated toxic activity; and (3) detecting in vitro a cytopathic effect in the permissive cell line.

The term '"stealth virus-associated toxin" or t"toxin" refers to the molecular entity (or entities) that mediates the toxic activity observed in stealth virus cultures in vitro, and which appears capable of suppressing stealth virus growth. Cultures with toxin are often more difficult to infect with other stealth viral isolates. The toxic activity is detectable in serum and cerebrospinal fluid from stealth virus infected patients and may mediate certain symptoms associated with the patient's illness.

In preferred embodiments the toxic activity is neutralized by frequently replacing the culture medium, using medium in which the production of the toxin is minimized, or by adding a neutralizing agent to the culture; the neutralizing agent is fetal calf serum or retinoic acid, an antibody specific for the toxin, or a chemical or virus derived agent capable of competing with or reversing the toxic activity; and the sample is derived from a human, animal, food, or other environmental substance or object.

The term "neutralized" refers to any amount of inhibition or decrease. Thus, by neutralizing the toxic activity, one actually increases the detection of stealth virus. The term "replacing" refers to removing old culture medium and transferring new culture medium into the sample being tested to a new culture medium.

Stealth viruses may be isolated from a sample of blood or other biological samples including surgical and fine needle aspiration tissue biopsies, post mortem organ biopsies, throat swabs and saliva, urine, cerebrospinal fluid (CSF), other body fluids, blood and blood products intended for transfusion or for in vitro uses, vaccines, foods, and from the environment.

In a third aspect, a method for detecting a stealth-virus is provided by: (1) inoculating a permissive cell line with a sample of the virus in a culture; (2) adding serum free medium to the culture; and (3) detecting in vitro the presence of a CPE in the permissive cell line.

In preferred embodiments, the serum free medium is medium X Vivo-15 (BioWhittaker, Inc., Walkersville, Md). X Vivo-15 is a Iscove's modified Delbecco's medium with the addition of human albumin, human insulin and human transferrin. Iscove's modification of Delbecco's medium is intended to support high density cell growth and has additional glucose, salts and vitamins compared to Delbecco's medium (Iscove and Melchers, *J. Experimental Medicine,* 147:923 (1963)). Albumin, insulin and transferrin are provided as a replacement for the need for serum. Since these proteins are of human origin, X Vivo-15 is suitable for growing human cells intended to be injected into autologous recipients.

Of several serum free media tested, medium X Vivo-15 was clearly superior to medium 199 plus 7% FCS for supporting stealth viral growth. The CPE developed more rapidly and there was less of a general loss of vitality seen with the usual stealth viral cultures. Medium X Vivo-15 was also found to be superior to other serum free media, for example, Aims-V medium from GIBCO BRL, Gaithersburg, Md. Aims-V medium also uses human albumin, insulin and transferrin, but the basic salt component is F-10 medium (Ham, *Exp. Cell Res.,* 29:515 (1963)), rather than Iscove's. X Vivo-15 was also superior to medium 199 plus bovine albumin, insulin and transferrin, with or without FCS.

In a fourth aspect a method of detecting a stealth virus is provided by: (1) co-centrifuging a sample of said virus with a permissive cell line of indicator cells; (2) inoculating the cell mixture into culture vessels; and (3) detecting in vitro a CPE in the permissive cell line.

Pre-culture centrifugation (PCC) of patients' lymphoid cells with indicator fibroblast cells refers to co-centrifugation of patients' or animals' lymphocytes with freshly harvested fibroblasts and replating the cells back into the original tubes containing the fibroblasts.

In preferred embodiments the method involves adding cytomegalovirus (CMV) supernatant, or viral enhancing medium, to the culture and frequently refeeding the culture medium. Viral enhancing medium (VEM) is derived from the supernatants from actively replicating viruses which are functionally related to the stealth virus. Filtered, boiled medium collected from a CMV positive MRC-5 cell line showing a well defined 2+ CPE was able to supplement the stealth viral growth enhancing activity of medium X Vivo-15 used alone and was designated VEM for "viral enhancing medium". Titration of this medium showed that 20%–30% was adequate to provide significant growth enhancement. X Vivo-15 medium containing 20% each of both CMV and HHV-6 supernatants was more effective than medium containing 20% or 30% CMV supernatant.

In a fifth aspect, a method of detecting a stealth virus is provided by: (1) inoculating a permissive cell line with a sample of said virus in a culture; (2) adding viral enhancing medium to the culture; and (3) detecting in vitro a CPE in the permissive cell line.

In preferred embodiments the viral enhancing medium contains 30% boiled, filtered products derived from the supernatant of cultures of cytomegalovirus and 70% medium X Vivo-15; and the cell line is maintained in a culture medium, that is frequently replaced.

In a sixth aspect culturing a virus is provided by: (a) cocentrifuging a sample of said virus with a permissive cell line of indicator cells; (b) inoculating the cell mixture into culture vessels; (c) adding viral enhancing medium to the culture; and (d) detecting in vitro a CPE in the permissive cell line.

The PCC step in combination with the use of VEM will also improve the detection of the CPE associated with cytomegalovirus (CMV) and human herpesvirus 6 (HHV-6). The growth of CMV and HHV-6, however, are less dependent on these modifications than that of stealth viruses. Furthermore, frequent refeeding of the cultures is not nearly as important for these viruses as it is for stealth viruses.

In preferred embodiments the virus is a stealth virus, cytomegalovirus, or human herpesvirus-6.

The summary of the invention described in detail above is not intended to limit in any way the scope of the present invention which is defined in the appended claims.

4. DETAILED DESCRIPTION OF THE INVENTION

Preferred embodiments of the present invention are described in detail below. However, the following description of the preferred embodiments is not intended to limit in any way the scope of the present invention, which is defined in the appended claims.

The present invention provides several culturing conditions that induce a cytopathic effect in a sample containing a stealth virus. These culturing conditions include using approximately 5%–10% fetal calf serum, refeeding the culture medium every 24 to 72 hours using viral enhancing medium and using preculture centrifugation. These conditions are important for inducing a cytopathic effect. For example, the failure to replace the culture medium every 24 to 72 hours often prevents detection of the cytopathic effect. Another example is provided by the fact that not all serum free medium induce a cytopathic effect. Indeed, the use of a basal medium such as minimal essential medium with 2% fetal calf serum and weekly refeeding of the cultures as is commonly practiced in most clinical virology laboratories will not yield a cytopathic effect with primary isolates of a stealth virus. Thus, it can be seen that only a carefully selected specific set of culturing conditions are capable of inducing a cytopathic effect in a sample containing a stealth virus.

5. UTILITY

The present invention provides methods for the detection of a stealth virus. A virus is an infective agent and the stealth virus is associated with disease. The disease may be chronic fatigue syndrome (CFS) or one of several other diseases. Therefore, my invention has broad application to any area in which it is important to detect a stealth virus. Such areas include medical, veterinary, and agricultural diagnostics and industrial and pharmaceutical biological quality control.

Many patients with a stealth viral infection have a stealth virus associated disease. Therefore, the detection of the presence of a stealth virus may allow one to confirm the diagnosis of a particular disease. Thus, those patients may avoid needless treatment, including psychiatric treatment. Indeed, it is useful to detect the stealth virus in order to develop a therapy or treatment for patients with a stealth viral associated disease. For example, in order to develop a vaccine it is useful to first detect the virus.

In contrast, many patients without a stealth viral infection do not have a stealth virus associated disease. Thus, the failure to detect a stealth virus may indicate a psychiatric rather than physiological problem. Therefore, those patients may seek proper treatment, such as psychiatric treatment, rather than pursuing treatment aimed at eliminating or reducing the effects of a stealth virus.

Since the stealth virus is associated with disease, it will often times be useful to detect the virus either in order to eliminate or avoid it. For example, in some circumstances a pure material or sample is desired and it would therefore be useful to detect a stealth virus in the material or sample.

It would be useful to know if a food or beverage contained a stealth virus. One could simply avoid consuming the food or beverage in that case as a matter of prudence in order to reduce the risk of contracting a stealth virus associated disease. Similarly, it would be useful to know if a sample of blood contained a stealth virus. One could then simply avoid that blood in order to reduce the risk of contracting a stealth virus associated disease. Many other potential sources of infection are identified herein. Thus, detecting the virus may allow individuals to avoid the virus and any diseases associated with the virus. In other words, the invention is useful for prevention of disease transmission by identifying potential sources of infection.

The present invention is also useful in a variety of other ways readily apparent to those skilled in the art.

6. EXAMPLES

This invention will be more fully understood with reference to the examples which follow. The following examples are intended to illustrate the invention, but not to limit its scope which is defined in the claims appended hereto. The following examples are presented to illustrate the advantages of the present invention and to assist one of ordinary skill in the art in making and using the same, but are not intended in any way to otherwise limit the scope of the disclosure or the protection granted by a letters patent hereon.

In the following examples, the detection of the cytopathic effect was recorded as follows. This minimal level of CPE has to be transferable to secondary cultures for the culture to be recorded as a true positive (+). A + (one plus) positive effect indicates the presence of multiple enlarged retractable cells forming small clumps with indistinct cell borders are clearly seen in the cultures. A ± (plus/minus) or equivocal effect refers to a minimal change in the culture in which the rounded cells are either not enlarged or non-refractile (possibly dead). Less than 4% of cultures from CFS patients have been recorded as equivocal, either because the CPE has been restricted to only a small region of the culture, or because it has failed to recur on secondary passage. These cultures have been excluded from analysis.

A ++ (two plus) strong positive response is recorded when vacuoles are clearly identified within enlarged, rounded, refractile cells and/or when multiple foci of cell clumping and/or destruction are apparent which are ringed by cells described as having a positive effect. A +++ (three plus) very strong positive effect refers to extensive ++ cellular changes throughout much of the culture and/or the appearance of large retractile vacuolated, foamy syncytial cell formation. Typical CPE's are shown in Patent Cooperation Treaty publication number WO 92/20787.

A benefit of using multiple indicator cell lines, is that the CPE appearances in the different cell lines sometime complement each other. For example, cell syncytia are usually best observed in monkey kidney cells. The smaller rounded refractile cells are usually best observed in the human fibroblasts. In over 80% of positive cultures, the CPE is clearly observable in at least 2 of the 3 cell lines. As with any viral induced CPE, it is important to confirm transmission to fresh cultures. In recipient cultures, the stealth virus induced CPE generally develops more rapidly than in the primary culture with at least the same level of intensity.

Although the appearances of the CPE share some features in common with those associated with cytomegalo-virus (CMV) and herpes simplex virus (HSV) infection, stealth virus cultures can be readily distinguished from cultures harboring these viruses. The CPE from HSV is much more rapid, occurring in a matter of days. The destruction is greater with large masses of dead cells. The CPE from CMV tends to initially develop in smaller, looser clusters and evolves more slowly than observed with stealth viruses. The intracytoplasmic vacuolization and syncytia formation are far less prominent with CMV than with stealth viruses. The stealth virus infected cells give more the appearance of "foamy cells" than does CMV. Indeed, with some stealth viral cultures, there appears to be a marked accumulation of lipid-like material attaching itself to the wall of the culture tube. Human CMV does a not infect monkey derived cells.

7. Example 1: Culture Of Stealth Viruses—7% FCS and Frequent Refeeding

Culture tubes containing human fibroblast (MRC-5), primary human foreskin fibroblast (MRHF) and rhesus monkey kidney (RMK) cells are each inoculated with a cellular mixture of the buffy coat granulocytes and ficoll-hypaque separated lymphocytes derived from approximately the equivalent of one milliliter (ml) of heparinized blood. Typically, 5 ml of blood collected into a "green top" heparinized tube, are layered onto 3 mls of a ficoll-hypaque lymphocyte separation medium. Following 20 minutes centrifugation at 1,500 rpm, the lymphocyte, which collect at the plasma:ficoll hypaque interface, and the "buffy coat", present on the top of the erythrocyte layer, are collected into approximately 1 ml. An effort is made to minimize the number of erythrocytes in collecting all of the visible buffy coat.

The cell mixture is washed once in 1 ml of 199 medium containing 7% FCS and resuspended into 1 ml. Aliquots of 0.2 ml of the cells are added to culture tubes containing 1 ml of 199 medium plus FCS. The tubes are placed in an incubator at 37° C. for 45–60 minutes. The are then rinsed to remove macroscopically visible erythrocytes and other non-adherent cells. Rinsing (washing) consists of emptying the fluid content of the culture tube by decanting or by aspiration; adding 2 mls of medium or phosphate buffer saline; rocking the tube for several seconds to suspend erythrocytes; decanting the tube again. This important step is performed 2–10 times or until there are no macroscopically visible erythrocytes.

Two mls of medium with 7% FCS, are added and the tubes returned to a 37° C. incubator. Cultures are maintained in the incubator at 37° C., with refeeding (replacement of old medium with medium) at 24, 48 and 72 hours. The tubes are examined microscopically after the 24 hour refeeding and, if residual erythrocytes are present, the tubes are rinsed in a manner similar to that performed at the 45–60 min. step. The tubes are refed three times each week by replacing the old medium with 2 mls of fresh medium. This procedure is designed to reduce the accumulation of a toxic component in the culture medium which tends to suppress viral growth. The tubes are examined three times per week for evidence of CPE (CPE). CPE is generally recognizable between 2–3 weeks after culturing.

A lack of regular refeeding of the cultures can result in a tendency for the CPE to abort and not to progress. This effect is not seen with CMV infected cultures. In unfed stealth virus cultures and even with regular refeeding, one can observe a toxic effect on many of the remaining cells. Culture cells appear to lose a degree of vitality and become duller in appearance compared to control cultures. The fibroblasts can assume somewhat of a pavement appearance, instead of the elongated shape. Some of these changes can be mimicked using 5 nM of the polyether marine toxin okadaic acid (Cohen et al., "Okadaic acid: A new probe for the study of cellular regulation" *Trends Biochem. Sci.*, 15:98–102 (1990). CMV positive cultures do not demonstrate the toxic activity such as that observed with stealth viruses.

Moreover, the detection of CPE from CMV is readily seen in cultures containing only minimal essential medium and 2% FCS even without regular refeeding of cultures. This is the routine medium used in most virology laboratories and can be contrasted with the more enriched medium 199 and 7% FCS that is used to culture stealth viruses. The more enriched medium and the higher concentration of FCS, help to neutralize the toxic, stealth virus growth inhibiting effects, which would otherwise occur in the cultures.

Although presumptive of stealth virus infection, the CPE appearance may require additional confirmation for a definitive conclusion of stealth virus infection.

8. Example 2: Viral Enhancing Medium (VEM)

In preparing viral enhancing medium a known positive CMV culture was passaged into a flask of MRC-5 cells and fed with X Vivo-15 medium. The cultures were observed for the development of CPE. The culture medium was changed at 1 week when approximately 50% of the cells showed signs of CPE, but before there was marked cellular destruction. This newly added medium was collected 48 hours later. It was centrifuged at 800 g for 20 minutes to remove cellular debris.

The medium was transferred to new tubes which were placed in a beaker containing water. The water was heated to boiling for 20 minutes. After cooling, the medium was filtered through a 0.45 micron Millipore filter. This material was diluted 30:70 into regular X Vivo-15 medium to constitute a "lot" of CMV derived VEM. Each lot of VEM is tested to confirm: i) that it does not contain any residual live CMV by adding the medium to MRC-5 cells; and ii) that it can promote the development of the CPE induced by the prototype stealth virus by comparing the growth of the stealth virus in RMK cells containing VEM with that of similarly inoculated cells containing X Vivo-15 medium without supplement.

VEM has been tested on ten additional stealth viral isolates and clearly enhanced the growth of all of them. Two of these isolates are known to share CMV related sequences with the prototype stealth virus. Another isolate (from patient G. P.) shares antigens with HHV-6, rather than CMV, and is considered an HHV-6 related stealth virus. Another isolate appears to have an adenoviral sequence. The use of VEM also reduced the time for a discernible CPE using fresh blood from two newly cultured CFS patients. It enhances the intensity of the CPE and reduces the tendency for weekly positive cultures to revert to near normal appearance. VEM has also worked well in the cultures from the tissues of cats inoculated with the prototype stealth virus from patient D. W. allowing for clearly positive culture results. VEM obtained from HHV-6 (strain GS) infected fibroblasts was similarly tested for its ability to promote the growth of CMV and HHV-6 associated stealth viruses. It worked well with both viral types with a discernable advantage on the HHV-6 related stealth virus from patient G. P., compared to the CMV related stealth virus from patient D. W.

As a specific example, cultivation of a prototype stealth virus isolated from a CFS patient (initials D. W.) can be greatly enhanced by the addition to the culture of VEM comprising a 30% concentration of boiled, filtered supernatants from cytomegalovirus (CMV) infected cultures. This addition helps remedy a deficiency of viral growth enhancing components coded for by the immediate-early (I-E) and probably other CMV related genes which are not detectable in the stealth virus from this patient.

9. Example 3: Viral Enhancing Medium and Pre-Culture Centrifugation

Human fibroblast (MRC-5), rhesus monkey kidney (RMK) and rabbit kidney (RK) cell lines were obtained from BioWhittaker, Inc., Walkersville, Md. The tubes were placed in a 37° incubator. The next day, the Delbecco's modified Eagles medium containing 2% FCS is replaced by medium 199 plus 7% FCS. The tubes were used to provide indicator cells for stealth viral cultures within the next 7 days. To establish the viral cultures, the contents of a single test tube of each of the indicator cell lines to be used were scraped from the tubes and washed once in X Vivo-15 medium.

The cells were gently resuspended into approximately 0.5 ml of medium and transferred to 2 ml Eppendorf tubes. Prior to this step, ficoll-hypaque separated lymphocytes from either heparinized or citrate treated whole blood, were obtained by layering 5 mls of anti-coagulated blood onto 3 mls of ficoll-hypaque solution in 12 ml conical tubes. The tubes were centrifuged for 20 min at 800 g. The banded lymphocytes were aspirated and transferred to a fresh tube for washing in 10 mls of medium. The lymphocytes were resuspended in approximately 1 ml. Aliquots of 0.2 ml of the lymphocytes were added to each of the Eppendorf tubes containing the harvested fibroblast indicator cells with a final aliquot stored for future studies.

The lymphocyte-fibroblast cell mixture was centrifuged at high speed for 3 minutes. The tightly-packed cell pellet was gently resuspended and transferred back to the tube from which the fibroblasts were originally obtained. Two mls of VEM (X Vivo-15 medium supplemented with 30% CMV supernatant) were added and the tubes are placed in an incubator at 37° C. The tubes were refed with VEM at 48 and 72 hours and thereafter 3 times per week.

Control cultures in which either lymphocytes from other individuals are used, or the fibroblasts were processed but with the exception of no added lymphocytes, were fed in parallel with the test cultures. Note, in this revised protocol, buffy coat granulocytes are no longer routinely used since the contaminating erythrocytes tended to clump about the fibroblasts during the centrifugation step and were difficult to remove in subsequent washing of the cultures. Granulocytes may be an important source of virus in some patients. If this proves to be so, leucocyte rich plasma will be obtained by dextran precipitation of the erythrocytes from anti-coagulated blood, or as an alternative, modifications of the ficoll-hypaque separation method can be used which will separate both lymphocytes and granulocytes away from the erythrocytes. For example by using PMN isolation medium from Robbins Scientific Corp., Sunnyvale Calif. CSF and tissue extracts can be used in place of the lymphocytes.

The cultures were observed for a CPE which characteristically consists of rounding and swelling of the cells, formation of cell clumps which tend to disperse, appearance of intracellular granules/vacuoles and an overall foamy cell appearance often with prominent accumulation of lipid-like material.

TABLE 3

Examples of the Enhanced Recovery and More Intense Development of CPE by a Stealth Virus from a CFS Patient Using Pre-Culture Centrifugation (PCC) and Viral Enhancing Medium (VEM).*

| Method of Culturing | Time to CPE** | Intensity of CPE |
| --- | --- | --- |
| Patient 1 | | |
| Medium 199 + 7% FCS | 45 days | 1–2+ |
| PCC and VEM | 12 days | 3+ |
| Patient 2 | | |
| Medium 199 + 7% FCS | 28 days | 1–2+ |
| PCC and VEM | 16 days | 3+ |

*Medium X Vivo-15 containing 30% supplement of boiled filtered supernatant from a CMV culture also grown in medium X Vivo-15.
**Results are in RMK cells. Enhanced growth was also seen in MRC-5 cells.

10. Growth of Stealth Virus in Insect Cell Line

The *Spodoptera fruiperda* derived ovarian cell line Sf9 that is used routinely for the propagation of recombinant insect baculovirus was obtained from PharMigen, San Diego. It was maintained at 27° C. in Grace's medium with 10% fetal calf serum. The stealth viruses from patients D. W., G. P., K. E. and B. B. were passaged into the insect cell line using 0.1 ml of cell-free supernatant from an infected MRC-5 human fibroblast culture. CPE was clearly seen within two days and progressed over the next several days.

The infected cultures showed enlarged foamy cell syncytia. Virus infectious for MRC-5 and for insect cell cultures was recoverable from the insect cell cultures to a dilution of $10^{-3}$ ml. Electron microscopic examination of the insect cultures infected with the virus from patient D. W. showed abundant herpes-like viral particles. In control studies, neither cytomegalovirus, human herpes virus 6, varicella zoster virus or Epstein-Barr virus induced CPE in the insect cell line; nor was infectious virus recoverable from these cultures.

11. Deposit Of Microorganisms

The stealth virus isolated from patient D. W. (virus-X infected MRC-5 cells) was deposited with the American Type Culture Collection (ATCC)—12301 Parklawn Drive, Rockville, Md. 20852, under the provisions of the Budapest Treaty on the International Recognition of the Deposit of Microorganisms for the Purposes of Patent Procedures on Sep. 17, 1991, and were assigned accession no. VR-2343.

The present invention is not to be limited in scope by the microorganisms deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety.

What is claimed is:

1. A method of detecting a stealth virus comprising culturing a sample under conditions in which any stealth virus in said sample is able to induce a cytopathic effect, thereby detecting said stealth virus.

2. The method of claim 1, in which the culturing is performed by:
   (a) inoculating a permissive cell line with a sample; and
   (b) detecting in vitro a cytopathic effect in the permissive cell line.

3. The method of claim 2, in which the cell line is maintained in culture medium, and further comprising replacing the culture medium every 24 to 72 hours.

4. The method of claim 1, in which the sample is taken from a patient diagnosed from physical symptoms as having chronic fatigue syndrome.

5. The method of claim 2, wherein the cell line is an insect cell line.

6. The method of claim 2, wherein the cell line is *Spodoptera fruiperda* isolated ovarian cell line Sf9.

7. A method for culturing a stealth virus comprising:
   (a) inoculating a permissive cell line with a sample;
   (b) neutralizing stealth virus associated toxic activity; and
   (c) detecting in vitro a cytopathic effect in the permissive cell line, thereby culturing said stealth virus.

8. The method of claim 7, in which the cell line is maintained in culture medium and the neutralizing comprises replacing the culture medium every 24 to 72 hours.

9. The method of claim 8, in which the cell line is maintained in culture medium and the neutralizing comprises adding a neutralizing agent to the culture medium.

10. The method of claim 9, in which the neutralizing agent is selected from the group consisting of 5% to 10% fetal calf serum in medium 199, an antibody specific for the toxin and a chemical agent capable of reversing the toxic activity.

11. The method of claim 7, wherein said sample is isolated from a human or animal source.

12. The method of claim 7, wherein said sample is isolated from food, or an object suspected as being a possible source of stealth viral infection or transmission.

13. A method of culturing a stealth virus comprising:
   (a) inoculating a permissive cell line with a sample of said virus in a culture;
   (b) adding serum free medium to the culture; and
   (c) detecting in vitro the presence of a cytopathic effect in the permissive cell line.

14. The method of claim 13, wherein the serum free medium is medium X Vivo-15.

15. A method for culturing a stealth virus comprising:
   (a) co-centrifuging a sample of said virus with a permissive cell line of indicator cells;
   (b) inoculating the cell mixture into culture vessels; and
   (c) detecting in vitro a cytopathic effect in the permissive cell line.

16. The method of claim 15, further comprising adding cytomegalovirus supernatant to the culture.

17. The method of claim 15, further comprising adding viral enhancing medium to the culture.

18. The method of claim 15, further comprising refeeding the culture medium every 24 to 72 hours.

19. A method for culturing a stealth virus comprising:
   (a) inoculating a permissive cell line with a sample of said virus in a culture;
   (b) adding viral enhancing medium to the culture; and
   (c) detecting in vitro a cytopathic effect in the permissive cell line.

20. The method of claim 19, wherein said viral enhancing medium contains 30% boiled, filtered products isolated from the supernatant of cultures of cytomegalovirus and 70% medium X Vivo-15.

21. The method of claim 19, in which the cellline is maintained in culture medium, and further comprising replacing the culture medium every 24 to 72 hours.

22. A method for culturing a virus comprising:
   (a) cocentrifuging a sample of said virus with a permissive cell line of indicator cells;
   (b) inoculating the cell mixture into culture vessels;
   (c) adding viral enhancing medium to the culture; and
   (d) detecting in vitro a cytopathic effect in the permissive cell line.

23. The method of claim 22, wherein said virus is a stealth virus.

24. The method of claim 22, wherein said virus is cytomegalovirus.

25. The method of claim 22, wherein said virus is human herpesvirus-6.

* * * * *